United States Patent [19]

Olmstead

[11] Patent Number: 5,607,119
[45] Date of Patent: Mar. 4, 1997

[54] DISPENSER

[76] Inventor: Arnold G. Olmstead, R.R. No. 4, Lakefield, Ontario, Canada, K0L 2H0

[21] Appl. No.: 543,796

[22] Filed: Oct. 16, 1995

[51] Int. Cl.$^6$ .......................... B65H 18/04; B65H 23/26; B65H 19/30

[52] U.S. Cl. ....................... 242/532.6; 242/533; 242/539; 242/546.1; 242/548.2; 221/199; 221/281; 221/303

[58] Field of Search .................. 242/532.6, 533, 242/533.7, 539, 546.1, 548.2, 538.2, 419, 419.4, 560, 560.3, 561; 221/303, 307, 309, 312 R, 312 B, 199, 175, 281

[56] References Cited

U.S. PATENT DOCUMENTS

| | | | |
|---|---|---|---|
| 1,287,163 | 12/1918 | Winter | 242/533 |
| 1,823,572 | 9/1931 | Reed . | |
| 1,902,826 | 3/1933 | Bobo | 242/546.1 |
| 2,571,175 | 10/1951 | Williams et al. . | |
| 2,974,839 | 3/1961 | Batlas et al. | 242/560 |
| 3,516,618 | 6/1970 | Reinke | 242/419.4 |
| 3,647,152 | 3/1972 | Trewella . | |
| 3,664,594 | 5/1972 | Novak . | |
| 3,946,964 | 3/1976 | Zinser | 242/532.6 |
| 4,061,287 | 12/1977 | Shakespeare | 242/548.2 |
| 4,280,672 | 7/1981 | Santos et al. | 242/532.6 |
| 5,060,880 | 10/1991 | Mayer | 242/533 |
| 5,143,252 | 9/1992 | Shi | 221/185 |
| 5,276,936 | 1/1994 | Corrigan | 15/256.5 |

*Primary Examiner*—John M. Jillions
*Attorney, Agent, or Firm*—Michael M. Sakovich

[57] ABSTRACT

A container for storing and dispensing rolled bandages comprises a pair of attached half shells that are separable for cleaning and disinfection purposes. Strips of flexible material are formed into rolls by a hand crank having a slotted shaft rotatably journalled in opposing front and back walls at one end of the container. In registry with the shaft, a slot disposed in an adjacent side wall admits and guides the flexible strips into engagement with the shaft. A guide member is slidably positionable within the side wall slot to accommodate flexible strips of different widths. The side wall slot also includes a sweep member to brush off any foreign matter clinging to the strips as they are rolled. Withdrawal of the hand crank when a roll is complete disengages the shaft from the roll which then drops from the slot end of the container to the opposite end thereof from which it may be dispensed.

10 Claims, 4 Drawing Sheets

DISPENSER

FIELD OF THE INVENTION

This invention relates to a bandage dispensing apparatus generally and, in particular, to such apparatus adapted to wind strip bandage materials into rolled bandages.

BACKGROUND OF THE INVENTION

Rolled bandages have many applications in the fields of human and veterinary medicine, as well as in various sports activities. Pressure bandages, for example, may be used to bind a wound or to temporarily immobilize an injured limb. Supports for injured knee and arm joints often comprise an elasticized rolled bandage which is wrapped around the affected member. Similar and other uses are found in athletics, one example of the latter being the bandaging of a boxer's hands to avert injuries thereto.

Equine leg injuries of a relatively minor nature frequently occur in the lower leg region between the fetlock and knee. Injuries such as scrapes, bruises and contusions are usually treated by wrapping the affected limb with a rolled bandage in an effort to prevent exacerbating the injury or to treat same with antiseptic solutions, liniments and the like. Liquids of this type may be applied by way of a pad held in place by the bandage or, in some instances, simply by applying the liquid directly through a wetted bandage.

Like bandages are also employed to prevent minor injuries during training sessions, in which case the bandage is used either with or without padding.

Bandage wrapping is facilitated by using small rolls thereof and overlapping the free ends of sequential rolls provides extra length as required. Large bandage rolls are generally avoided because they are awkward to use and involve cutting which produces bandages of short and unequal lengths. In equine applications irregular, short bandage lengths result in excessive handling which, in the case of a skittish animal, may place it and its handler at risk of injury.

Preferably a bandage roll can be held in one hand, which imposes a size limitation on roll diameters. Furthermore, since a smaller diameter results in a greater number of individual rolled bandages, carrying a quantity of such bandages becomes problematic.

Reusing bandages, common in sports activities, physiotherapy and the like, necessitates rerolling which requires either hand rolling, a rather slow and tedious task, or recourse to a bandage rolling device of a type disclosed in U.S. Pat. No. 2,571,175 Williams et al, U.S. Pat. No. 3,647,152 Trewella and U.S. Pat. N. 3,664,594 Novak. Bandage rollers described in these patents are expected to perform well for bandages of a fixed width. However, bandages of different widths, as are required from time to time, are not rolled effectively because of the tendency of narrow bandages to wander along the shaft of a winding crank assembly. The result is a skewed roll which can jam within the bandage roller.

SUMMARY OF THE INVENTION

Having regard to the aforedescribed problems associated with rolled bandages, a principal provision of the present invention is a dispenser having utility in rolling bandages from a fresh fabric strip as well as from an unwound, previously used bandage roll.

Another provision of the invention is a container shell for storing a plurality of rolled bandages combined with a bandage rolling apparatus so that the bandages may be rolled and stored within the same container.

Yet another provision of the invention is a dispenser having a sweep member for frictionally engaging at least one surface of the strip to brush off any foreign material adhering thereto as the strip is rolled.

A still further provision of the invention is a storage container having an open dispensing end from which individual ones of rolled bandages may be extracted.

The problems associated with the prior art may be substantially overcome and the foregoing provisions achieved by recourse to the invention which relates to a dispenser that comprises, in combination, a longitudinally extended shell having a receiving end and an open discharge end, a slot disposed in a side wall of the shell adjacent the receiving end, a shaft rotatably journalled in opposing side walls of the shell adjacent the receiving end and in substantial registry with the slot and a guide member operable interactively with the slot and shaft for guiding a strip of flexible material through the slot into predetermined engagement with the shaft.

BRIEF DESCRIPTION OF THE DRAWINGS

The invention will now be more particularly described with reference to an embodiment thereof shown, by way of example, in the accompanying drawings in which.

DETAILED DESCRIPTION OF THE PREFERRED EMBODIMENT

Figure 1:
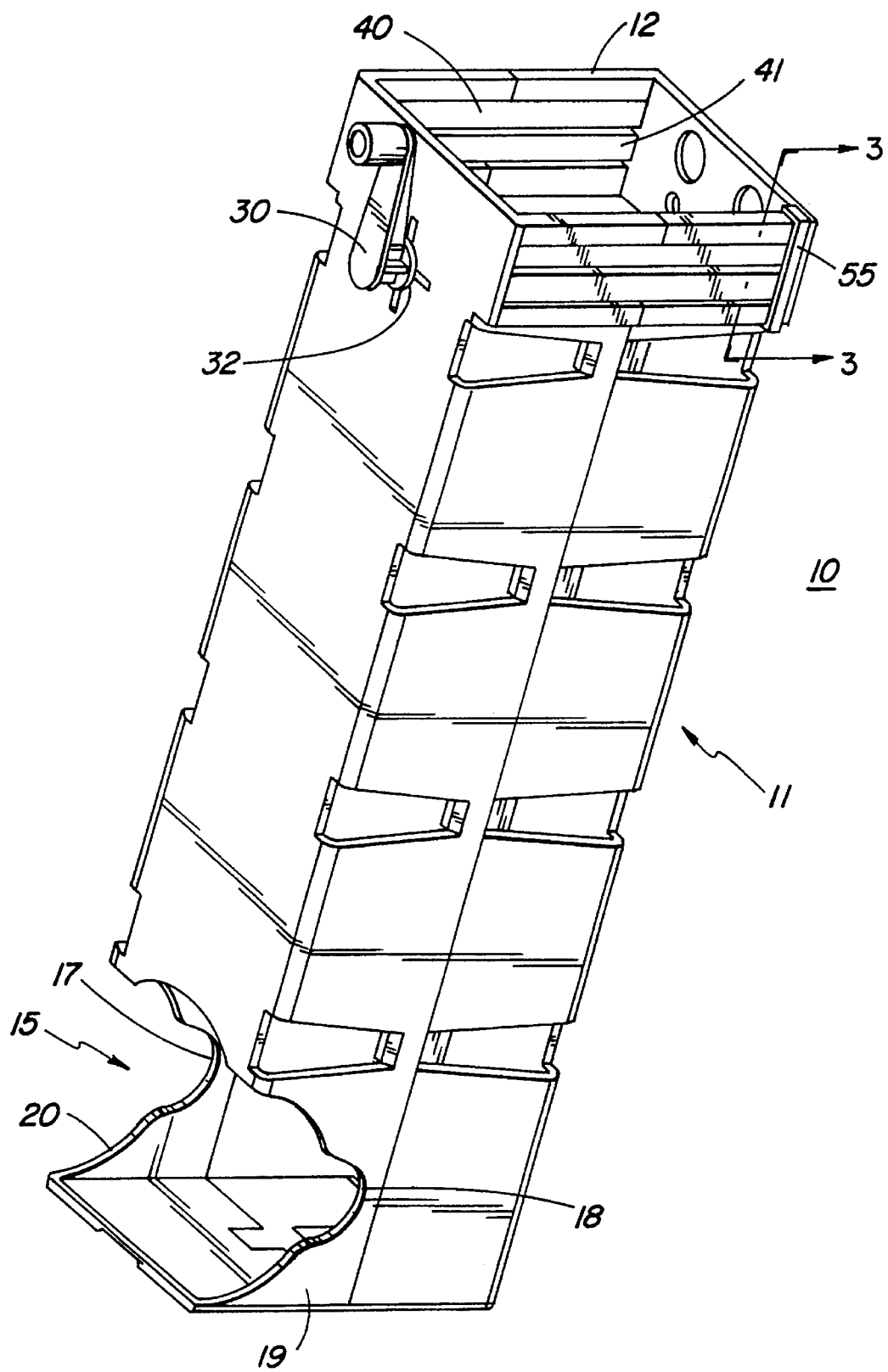
FIG. 1 is a front perspective view of a bandage dispenser in accordance with the invention.
Figure 2:
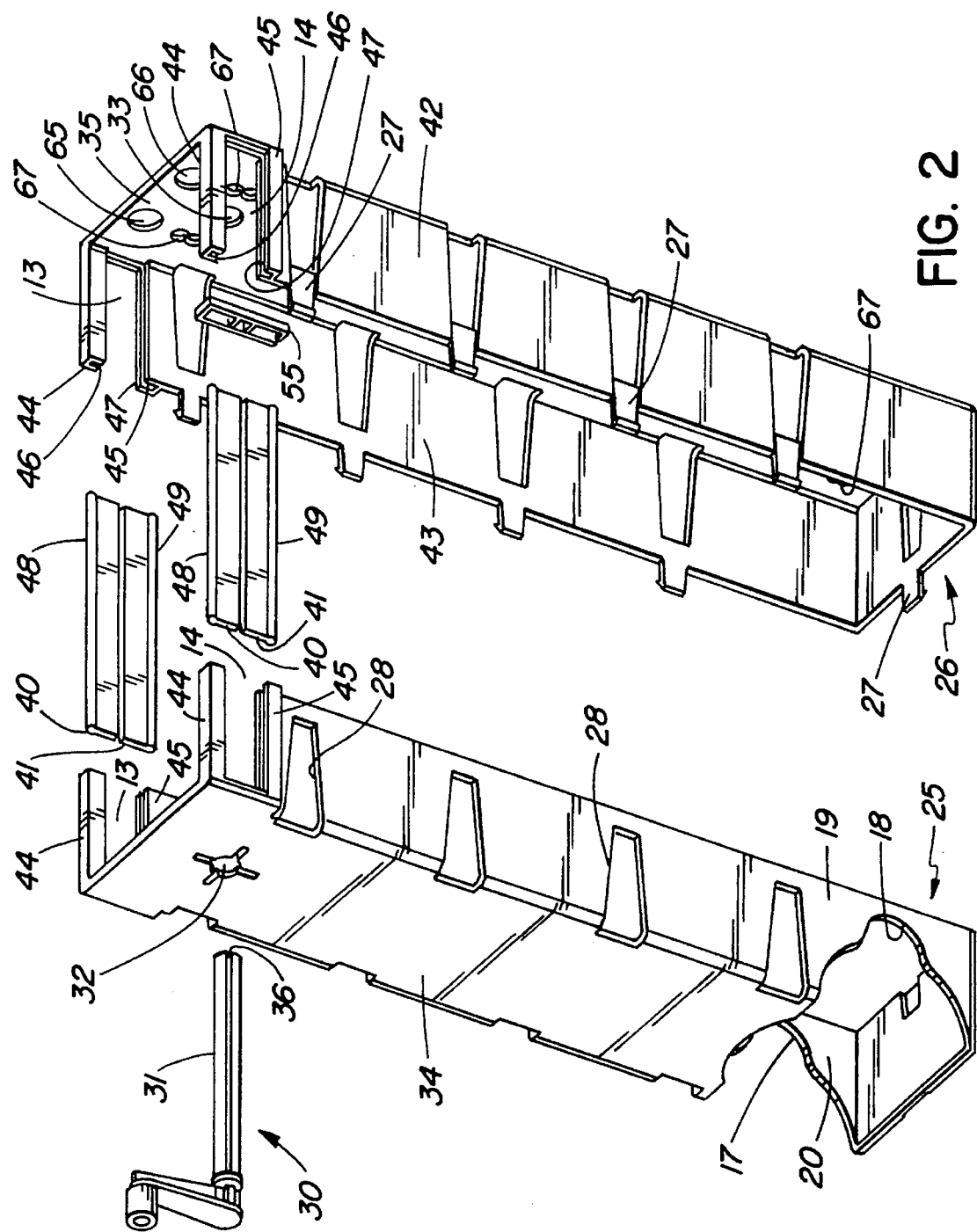
FIG. 2 is an exploded view of the dispenser shown in FIG. 1.
Figure 4:
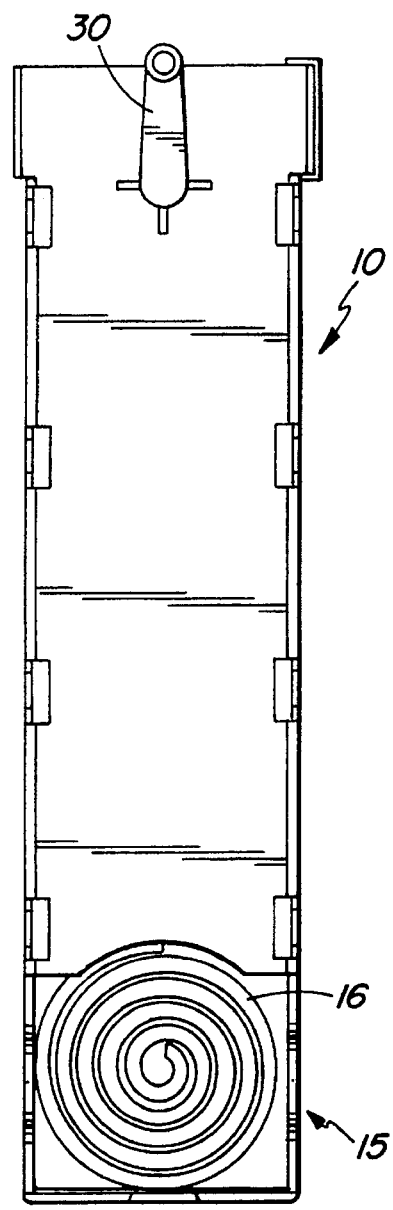
FIG. 4 is a front elevation view of the dispenser of FIG. 1 showing the placement of rolled bandages stacked therewithin.

A perspective view of a bandage dispenser 10 in accordance with the present invention is illustrated in FIG. 1. As shown, the dispenser comprises a longitudinally extended shell 11 having a receiving end 12 where strips of flexible bandage fabric are received through one of a pair of slots 13 and 14 (FIG. 2). A bottom end of the shell 11 has a dispensing opening 15 from which individual ones of bandage rolls 16 (FIG. 4) may be withdrawn. Bandage roll withdrawal is facilitated by recesses 17 and 18 formed in a pair of opposing side walls 19 and 20 in the shell 11. Having regard to FIGS. 1 and 2, it will be seen that the shell 11 comprises two half shells 25 and 26 that are held together in assembled relation by means of a plurality of hooks 27 in the half shell 26 which engage corresponding slots 28 in the half shell 25.

Bandages are wound into rolls 16 at the receiving end 12 by means of a hand crank 30 having a shaft 31 that is rotatably journalled in a pair of apertures 32 and 33 disposed in respective front and back walls 34 and 35 of the shell 11. It will be observed that the shaft 31 includes a slot 36 along a substantial portion of the shaft length. The slot 36 is open at the free end of the shaft 31 to facilitate rolled bandage removal by withdrawing the shaft therefrom.

The purpose of the slot 36 is to facilitate winding bandages about the shaft 31. Thus, a leading end of an unwound bandage, or any strip of flexible bandage material, inserted through one of the slots 13 or 14 is further inserted into the slot 36. Thereafter, rotation of the crank 30 winds the strip about the shaft 31 and continued operation of the crank 30 results in a bandage roll 16. Upon completion of the roll 16, the crank 30 is withdrawn through the aperture 32, whereupon the roll 16 falls to the bottom of the shell 11 (FIG. 4) where it is available to be dispensed at the opening 15.

Under normal conditions of use, either fresh bandage material, or former reusable bandage rolls that have been unwound, are wound into rolls 16 as described. As reused bandages may be recovered from a stable floor, or perhaps an outdoor paddock, foreign matter in the form of grit, bedding straw, hay and the like will be found adhering to one or both surfaces of the bandage strip. Removal of foreign debris is desirable and is provided in the dispenser 10 using an opposing pair of sweep members 40 and 41 which are disposed within each one of the slots 13 and 14, although only one slot need be so equipped.

Figure 3:
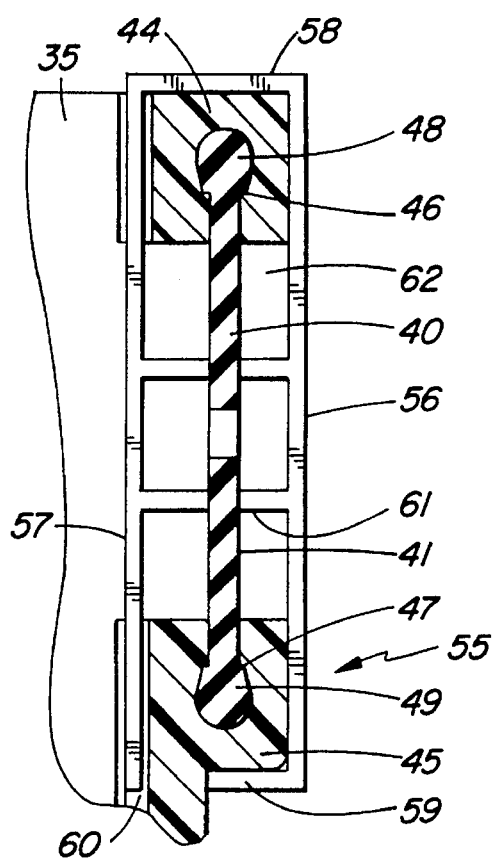
FIG. 3 is a cross-sectional view of a sweep assembly taken along the lines 3—3 in FIG. 1.

It will be observed in FIGS. 1 and 2 that the side walls 19 and 20 in the half shell 25 and corresponding side walls 42 and 43 of the half shell 26 include a pair of spaced apart retainers 44 and 45 having grooves 46 and 47, respectively, into which the members 40 and 41 are inserted. A cross-sectional view of the members 40 and 41 and their respective retainers 44 and 45 is shown in FIG. 3. Each member 40 and 41 is held captively within a respective groove 46 and 47 of its corresponding retainer 44 and 45 by means of an expanded edge 48, 49 as illustrated.

It will be understood that the members 40 and 41 are fabricated from an elastomer having free edges that flex to admit a strip of bandage material and allow the bandage strip to be drawn between the sweep members which provide an effective cleaning action while permitting the material to be rolled readily about the shaft 31. A further benefit derived from the use of an elastomeric product in the fabrication of the sweep members is a coefficient of friction sufficient to ensure a constant tension on the bandage strip as it is wound, thereby providing a tight and less bulky bandage roll 16.

Since equine leg bandages commonly vary in width from about 3 inches to 5 inches, a guide 55 is slidably disposed along one of the slots 13 and 14 and functions to guide the bandage strip as it is wound about the shaft 31. As illustrated in FIGS. 1 and 2, the guide 55 is held captive within the slot 14 and may be positioned at any point therealong to define the slot width.

Figure 5:
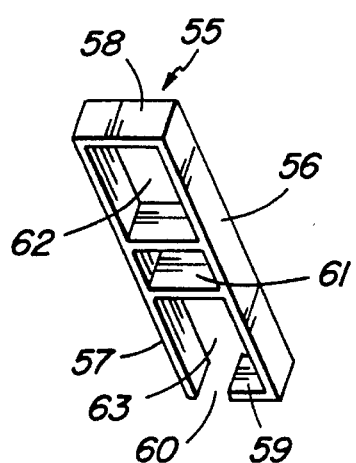
FIG. 5 is an enlarged perspective view of a bandage roller guide illustrated in FIG. 1.

An enlarged perspective view of the guide 55 is shown in FIG. 5. The guide 55 comprises two side walls 56 and 57, an upper end wall 58 and a partial bottom wall 59 having an open portion 60. A central web 61 joins the two side walls as illustrated and is in spaced relation with the end walls to define passages 62 and 63. Assembled in captive relation with the slot 14 as shown in FIGS. 1 and 3, it will be observed that the retainer 44 slidably passes through the passage 62 whereas the retainer 45 slidably passes through the passage 63 to permit positioning the guide 55 along the slot 14 between the members 40 and 41. Due to the flexibility of the members 40 and 41, the web 61 readily moves between the members but also functions to hold the guide 55 in place. As previously noted, the guide 55 permits bandages to be wound uniformly and avoids the problem of lateral bandage displacement that would result in a skewed, nonuniformly rolled bandage. Such a bandage can jam within the shell 11 and not drop down to the discharge opening 15 when the shaft 31 is withdrawn.

The shell 11 is preferably fabricated from a suitable plastic material in the form of the two half shells 25 and 26 that are clipped together as described to permit disassembly of the shell for effective cleaning and disinfection. Additionally, the slots 28 formed in the side walls of both half shells promote air circulation to assist in drying wet bandages and, by so doing, to increase the service life of a bandage.

The dispenser 10 may be conveniently carried by utilizing a pair of apertures 65 and 66 through which two fingers of a user may be inserted. These apertures may also be used for temporarily hanging the dispenser 10 from a peg or hook set in a wall (not shown). Alternatively, if a permanent wall installation is desired, an arrangement of keyhole slots 67 are provided in the back wall 35 for mounting purposes.

Figure 6:
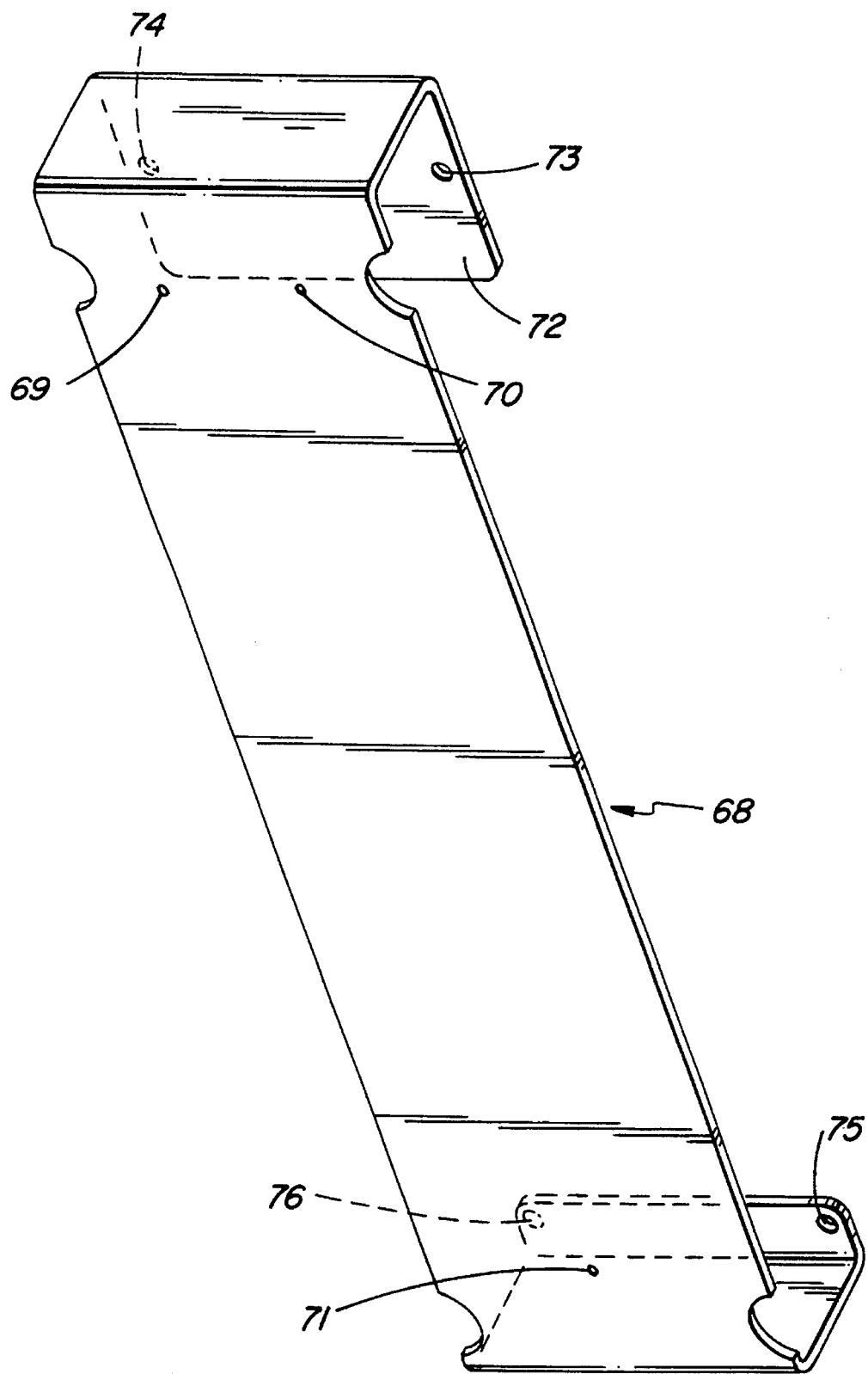
FIG. 6 is a perspective view of a bracket for wall mounting the dispenser of FIG. 1.

A separate wall mounting bracket 68 illustrated in FIG. 6 is used for mounting the dispenser 10 in spaced relation with the wall (not shown) to facilitate bandage winding and withdrawal of the rolls 16. The overall dimensions of the bracket 68 correspond generally to the dispenser 10, including the location of apertures 69, 70 and 71 which permit attachment to the dispenser at its keyhole slots 67 using known fasteners. A hook 72 portion of the bracket permits the attached dispenser 10 to be suspended from a horizontally positioned structural member of a fence, stall or building and is dimensioned accordingly. Apertures 73, 74, 75 and 76 are provided for a more permanent installation of the dispenser on the wall (not shown) using known fasteners.

To those skilled in the art to whom this specification is addressed, it will be apparent that the embodiment aforedescribed may be varied to meet particular specialized requirements without departing from the true spirit and scope of the invention disclosed. For example, although resilient, elastomeric sweep members 40 and 41 have been described, stiff bristle brushes may be readily substituted for such members to provide the same or similar benefits. Furthermore, although the dispenser 10 is preferably manufactured using the two half shells 25 and 26 as disclosed, the dispenser could be fabricated from a unitary cylindrical extrusion of predetermined cross-section either with or without side wall slots or apertures for ventilation purposes. The foregoing embodiment is therefore not to be taken as indicative of the limits of the invention, but rather as an exemplary structure thereof which is described by the claims appended hereto.

The embodiments of the invention on which an exclusive property or privilege is claimed are defined as follows:

1. A dispenser, comprising in combination:

a longitudinally extended shell having a receiving end and an open discharge end;

a slot disposed in a side wall of the shell adjacent the receiving end;

a shaft rotatably journalled in opposing side walls of the shell adjacent the receiving end and in substantial registry with the slot; and a guide member operable interactively with the slot and the shaft for guiding a strip of flexible material through the slot into predetermined engagement with the shaft.

2. A dispenser as claimed in claim 1, further comprising a sweep member disposed on the side wall in registry with the slot for frictionally engaging at least one surface of the strip to brush off any foreign material adhering to the surface as the strip is guided through the slot to the shaft.

3. A dispenser as claimed in claim 2, wherein the guide member is captively disposed within the slot to adjust the length thereof.

4. A dispenser as claimed in claim 3, wherein the guide member is slidably disposed within the slot.

5. A dispenser as claimed in claim 4, further comprising a rotatable handle attached to one end of the shaft.

6. A dispenser as claimed in claim 5, wherein the shaft is slotted to receive a free end of the strip guided through the slot.

7. A dispenser as claimed in claim 6, wherein the shell comprises a pair of half shells that are separably attached.

8. A dispenser as claimed in claim 7, wherein the shell includes a plurality of side wall ventilation apertures.

9. A dispenser as claimed in claim 8, wherein the sweep member comprises an opposing pair of elastomeric strips having flexible free edges.

10. A dispenser as claimed in claim 8, wherein the sweep member comprises an opposing pair of stiff bristle brushes.

* * * * *